United States Patent [19]

Blum

[11] 4,259,508

[45] Mar. 31, 1981

[54] NEW DERIVATIVES OF CYSTEINE

[76] Inventor: Jean Blum, 20 ter.rue de Bezons, Courbevoie, France, 92400

[21] Appl. No.: 957,487

[22] Filed: Nov. 3, 1978

Related U.S. Application Data

[63] Continuation of Ser. No. 760,913, Jan. 21, 1977, abandoned.

[30] Foreign Application Priority Data

Jan. 23, 1976 [FR] France ............................... 76 01837

[51] Int. Cl.³ .................... C07D 333/24; A61K 31/38
[52] U.S. Cl. ....................................... 549/72; 549/59; 549/60; 424/275

[58] Field of Search .................. 260/332.2 A; 549/59, 549/60, 72

[56] References Cited

U.S. PATENT DOCUMENTS 4,011,240  3/1977  Mauvernay .................. 260/332.2 A Primary Examiner—Alan Siegel

[57] ABSTRACT

This invention relates in the free form or in salts or esters form, new N,S-diacyl-L-cysteines in which at least one of the acetylating radicals is 2-thenoyl radical and particularly N-acetyl, S-2-thenoyl cysteine and its esters. A process for manufacturing those new cysteines is claimed, as their utilization in therapeutic and cosmetological grounds.

4 Claims, No Drawings

NEW DERIVATIVES OF CYSTEINE

This is a continuation of application Ser. No. 760,913, filed Jan. 21, 1977.

This invention relates in the free form or in the salts or esters, new N,S-diacyl-L-cysteines where at least one of their acylating groups is 2-thenoyl. Their formula is either

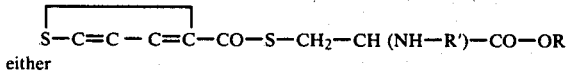

either

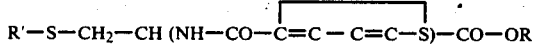

where R is a hydrogen atom or an alkyl radical and R' an acyl radical.

This invention concerns also a new process for manufacturing these new cysteines and their utilizations in human and animal therapy and in cosmetology.

Cysteine itself and several derivatives thereof, as S-carboxy methyl-cysteine or N-acyl-cysteine, are already known in therapy and cosmetology.

A newly issued patent application claims also the utilization of N-1-thenoyl-L-cysteins in therapy, but this compound is very unstable because of its free mercaptan group and it looses its activity during storage or administration.

The new cysteines of the invention may be directly manufactured from cysteine in free or salt forms, in a wet solvent or in water. For example, cysteine is dissolved in water and when pH is maintained between 5 and 9 with the addition of such reagent as sodium hydroxide or sodium hydrogen carbonate, a first N-acetylating reagent such as acid chloride or anhydride is gently added dropwise with stirring at a low temperature. At the end of the reaction, unreacted acylating reagent may be extracted out, for instance with benzene, and when rising eventually pH with an alkaline material, a second S-acylating reagent is gently poured with stirring.

Unreacted reagent may also be extracted out and the aqueous layer is precipitated by the adjunction of acid, for instance hydrogen chloride, until pH reaches 4 or 3. An oil is generally obtained which crystallizes more or less rapidly.

In the case of the N,S-di-thenoyl-cysteine, thenoyl chloride, for instance, may be added in a sole step, preferably at a pH over 9. This new process of selective N-acylation of cysteine followed by S-acylation without isolation of the intermediate is quite unforeseeable, even if the inventor has recently promoted an analogous process for homo-cysteine derivatives, as in this instance he thought the mercaptan function protected from the first acetylation by the thiolactone grouping.

Moreover, it is well known that N,S-diacetylcysteinate of methyl is manufactured from methyl-cysteinate at a pH neighboring 6.

Of course, water has no critical function in the process and it may be provided by other solvents, even anhydrous, but in the presence of an acid acceptor such as triethylamine. Most convenient temperatures are from room temperature to reflux of the chosen solvent, for instance acetone.

In one embodiment of the invention, a monoacyl cysteine, generally an N-acyl-cysteine may be used as raw material which is once more acylated in aqueous or anhydrous conditions as here above mentioned.

The di-acyl-cysteine esters of the invention are manufactured either by acylation of free or monoacylated cysteine esters, either by esterification of N,S-di-acyl-cysteines in the chosen alcohol in the presence of a strong acid, for instance hydrogen chloride.

For instance, an N,S-di-acyl-cysteine is dissolved in a HCl saturated anhydrous alcohol and the mixture is allowed to react, preferably at moderate temperature under a constant stream of anhydrous HCl.

Along another embodiment, N,S-di-acyl-cysteines are obtained by soft hydrolysis of N,S-di-acyl-cysteine esters, in alkaline condition, such for instance in a cold 5% sodium hydroxide solution.

The invention is illustrated by the following examples, without being confined to them.

EXAMPLE 1: N-acetyl-S-2-thenoyl-cysteine (ATC) from N-acetyl-cysteine 1 g of potassium hydroxide is dissolved into 15 ml of water and when chilling to 5°-10° C., 1.80 g acetyl-cysteine is added, then with vigorous stirring and dropwise, 2 g of thenoyl chloride dissolved in 10 ml of ether (10 minutes).

The mixture is allowed to react for 15 minutes is washed three times with 20 ml of ether. The aqueous layer is precipitated by adding 5% HCl until pH 2. Crude ATC is at first in an oil form, which crystallizes when washing three times with 1 Cml ether. It is dissolved into hot ethanol and decolorized with carbonblack.

20 ml of water is added to the filtrate and in the mixture allowed to stand in the cool. Pure ATC crystallizes as white crystals melting at 173° C. on the Kofler bank.

EXAMPLE 2: ATC from N-acetyl-S-2-thenoyl-cysteine of methyl 2 g of the raw material are strongly stirred in a 5% sodium hydroxide solution at the temperature of 40° C. Dissolution is complete within 10 minutes. The mixture is chilled, filtered and 5% HCl is added until complete precipitation of crude ATC which is recrystallized as in the above example.

EXAMPLE 3: ATC from cysteine 2.18 g of cysteine are dissolved into 20 ml of distilated water and chilled to 5°-10° C.

To this mixture are added together under vigorous stirring and dropwise, 2.2 g of acetic anhydride dissolved in 20 ml of ether and 2 g of hydrogen sodium carbonate in 30 ml of water as to maintain the pH between 7 and 8.

At the end of additions (10 minutes), the mixture is allowed to stand at 10° C. for 10 more minutes when stirring and is washed three times with 10 ml ether portions. 1.44 g sodium hydroxide dissolved in 20 ml distilated water are added to the aqueous layer and the temperature is fixed between 10 and 15° C. 3 g of thenoyl chloride in 20 ml ether are then added when stirring. Reaction and isolation of ATC are ended as indicated in the above example 1.

EXAMPLE 4: ATC from N-acetyl cysteine in anhydrous medium 1.80 g N-acetyl-cysteine are dissolved into 10 ml dry acetone. 1.1 g triethylamines, then 3.2 g thenoyl chloride dissolved in 10 ml dry acetone are then carefully added. The mixture is refluxed for 2 hours and triethylamine chloride is filtered. From the filtrate, acetone is evaporated under reduced pressure and the residue which is crude ATC is washed three times with ether. Purification and recrystallization are made as above.

EXAMPLE 5: N-acetyl-S-2-thenoyl-cysteinate of methyl from N-acetyl-cysteinate of methyl As in the above example 4, using N-acetyl-cysteinate of methyl instead of N-acetyl-cysteine. Recrystallization in ethyl acetate leading to white crystals melting at 122° C. on the Kofler bank.

EXAMPLE 6: N-acetyl-S-2-thenoyl cysteinate of ethyl from ATC.

1.5 g ATC are dissolved into 15 ml water free ethanol by heating at 50° C. and when holding this temperature for 3 hours, a slow stream of anhydrous HCl is allowed to bubble into the reaction flask.

At the end of this time, the flask is stoppered and the mixture allowed to react at room temperature for 12 hours. Alcohol is then evaporated under reduced pressure. The residual oil is washed with a 5% sodium hydrogen carbonate solution. Crude product crystallizes and it is purified in the mixture toluene-cyclohexane (65-35). White crystals melting at 90° C. on the Kofler bank.

Along here above example 6, the methyl ester of ATC was manufactured as its following esters:

| Examples: | MP °C.(Kofler) | Recryst. Solvent |
| --- | --- | --- |
| 7 - Isopropyl | 106 | Toluene - Cyclohexane |
| 8 - 2 Chloroethyl | 116 | Toluene |
| 9 - n-butyl | 97 | Toluene - Cyclohexane |
| 10 - iso-butyl | 102 | Toluene - Cyclohexane |
| 11 - t-butyl | Oil which decomposes when distillating | |
| 12 - octyl | Oil which decomposes when distillating | |

EXAMPLE 13: N,S-di-2-thenoyl cysteine 3.15 g of cysteine chlorhydrate monohydrate are dissolved into a 60 ml 10% sodium hydroxide solution. When chilling under 15° C., 6 g of thenoyl-chloride are added dropwise with efficient stirring. When the mixture becomes homogeneous, it is still allowed to stand for 15 minutes between 10° and 15° C. Then HCl is poured until pH 2-3. A gummy precipitate is washed with water, then with ether and crystallization occurs. Recrystallization in the mixture isopropanol-ethanol (50/50). White crystals melting near 112° C. (Kofler bank).

EXAMPLE 14: N-benzoyl, S-2-thenoyl-cysteine 3.51 g cysteine chlorhydrate monohydrate are dissolved into 40 ml water and 9 g NaHCO$_2$, are gently added, the mixture cooled to 15° C. and 2.85 g benzoyl chloride added dropwise with stirring (temperature between 15°-17° C.). The mixture is allowed to stand for 30 more minutes. 4.1 g dissolved in 10 ml water are then added. The mixture is cooled to 10° C. and 3 g thenoyl chloride are added dropwise with stirring. The mixture is allowed to stand for 15 minutes more and is then filtered and HCl is poured until pH 1. The precipitated oil crystallizes after standing for 48 hours in the refrigerator. It is washed with water and ether.

Recrystallization: toluene-ethanol (90-10)
White crystals melting at 145° C. (Kofler bank)

EXAMPLE 15: N-succinyl, S-2 thenoyl-cysteine

As in the above example 3, using succinic instead of acetic anhydride.
Recrystallization: water-ethanol (30-10)
White crystals melting 147°-8° C. (Koffler)

EXAMPLE 16: N-3-chromone-carbonyl-S-2-thenoyl-cysteine

As in the above example 8, using 2-chromonecarbonyl instead of benzoyl chloride.
Recrystallization: acetic acid
White crystals melting 213° C. (Kofler)

EXAMPLE 17: N-benzoyl-S-2-thenoyl-cysteinate of methyl

As in example 6, using ethanol instead of methanol and N-benzoyl,S-2-thenoyl-cysteine instead of ATC.
Recrystallization: methanol
White crystals M.P. 143° C. (Kofler)

EXAMPLE 18: N-benzoyl-S-2-thenoyl-cysteinate of 2-propyl

As in the above example 17, using isopropanol instead of methanol.
Recrystallization: water-isopropanol (30-70)
White crystals M.P. 112° C. (Kofler)

EXAMPLE 19: As in the above example 14, inversing the order of additions of thenoyl and benzoyl chlorides
Recrystallization: isopropylic ether
White crystals M.P. 90° C. (Kofler)

To illustrate the pharmacological and therapeutical properties of the new cysteines of the invention, the following data are given as non-limitative examples.

ATC was compared to S-carboxy-methyl-cysteine (SCMC) along the Quevarviller and Vu Ngoc technic inhalation of $SO_2$ by Rats which promotes hyper secretion of the intro-bronchitic mucus. At the end of the experimentation, lungs and bronchi of sacrified animals are examined. Then, 40 female Wister Rats are exposed 2 to 4 hours a day for a total exposure of 110 hours in a 400 ppm $SO_2$ atmosphere. The 4 first weeks (65 h exposition) the animals received no extra treatment. The 4 next week (45 h exposition) the animals received a daily dose of 500 mg/kg either of SCMC either of ATC (both per os).

Resulting data of lungs and bronchi examination are summarized in the joined table. It shows that ATC is quite active as a mucolytic agent. Moreover the mortality study shows the profitable effect of the treatment.

0% for ATC treated animals
13% for SCMC treated animals
27% for bronchitic reference animals These data were confirmed by the fact it was not possible to obtain any death by a single per os administration of ATC until 5 g/kg to Mice when in the same conditions, SCMC possesses a LD 50 surrounding 3.5 g/kg.

These very hard experimentations show that ATC is harmless and possesses a high mucolytic activity and is able to regenerate pulmonary and bronchic tissues when damaged by $SO_2$. ATC is then a precious medicine for the treatment of bronchitis, of cough and generally pulmonary affections promoted by pollution, bad weather or microbial and viral diseases.

It may be prescribed to a child at a daily dose from 100 to 1500 mg and to grown up persons from 200 to 3000 mg, doses that may eventually be increased because of the hazardlessness of the product.

ATC was also tried with success as trophic agent for skin, hair and nails and may be added in a cosmetological composition as a skin, hair or nail emollient, or as antiscurf element. For oil compositions, for instance for sun or anti-UV compositions, ATC esters may be chosen instead of ATC itself.

The present invention also concerns pharmaceutical and cosmetological forms associated. The concerned pharmaceutical forms may be used for oral, parental, local or rectal administration, in otorhinolaryngology and ophthalmology.

As non-limitative examples, gelatin-coated pills with 150 mg ATC were confectioned for adults using 3 to 6 units per day and a flavored and sweetened syrup at the dose of 5% of ATC was confectioned for children using 2 to 5 teaspoons per day depending on their age.

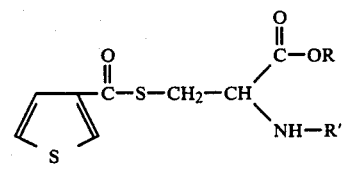

and a compound having the formula:

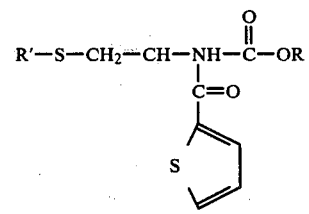

|  | LUNG EXAMINATION | | | | MAIN BRONCHIA EXAMINATION | | | | | SECONDARY BRONCHIA EXAMINATION | | | |
|---|---|---|---|---|---|---|---|---|---|---|---|---|---|
| Rats N° | Average weight | Pulmonary hypertropic | Bronchial diameter | Peri-bronchial Hyperplasy | Muquous veil | Noda mass | Compact stopper | Partial obstructions | Total obstructions | Muquous veil | Modal mass | Compact stoppers | Total obstruction |
| HEALTHY REFERENCE ANIMALS | | | | | | | | | | | | | |
| 1 to 10 | 263,5 | 0 | 145 | 1,15 | 0% | 0% | 0% | 0% | 0% | 0% | 0% | 0% | 0% |
| BRONCHITIC REFERENCE ANIMALS | | | | | | | | | | | | | |
| 11 to 25 | 198,5 | 0,97 | 200 | 1,60 | 90% | 67% | 30% | 73% | 37% | 100% | 83% | 17% | 83% |
| BRONCHITIC ANIMALS + SCMC | | | | | | | | | | | | | |
| 26 to 40 | 238,5 | 0,67 | 186 | 1,90 | 53% | 27% | 7% | 37% | 7% | 63% | 27% | 0% | 20% |
| BRONCHITIC ANIMALS + ATC | | | | | | | | | | | | | |
| 41 to 50 | 255 | 0,25 | 184 | 1,60 | 75% | 30% | 0% | 30% | 5% | 85% | 35% | 0% | 15% |

The embodiments of the invention in which an exclusive property or privilege is claimed are defined as follows:

1. A compound selected from the group consisting of a compound having the formula:

wherein R is selected from the group consisting of hydrogen and an alkyl group containing 1 to 8 carbon atoms and R' is selected from the group consisting of acetyl, benzoyl, thienyl, 2-chromone-carbonyl and succinyl, and pharmaceutically acceptable salts thereof.

2. A compound as defined in claim 1 wherein R' is thienyl.

3. A compound as defined in claim 1 wherein R is hydrogen.

4. The N-acetyl-S-2-thenoyl cysteine and its salts.

* * * * *